United States Patent
Pottier et al.

(10) Patent No.: US 11,229,705 B2
(45) Date of Patent: Jan. 25, 2022

(54) COATED NANOPARTICLES FOR USE FOR MODULATING ELECTRICAL POLARIZATION OF NEURONS

(71) Applicant: NANOBIOTIX, Paris (FR)

(72) Inventors: Agnès Pottier, Paris (FR); Laurent Levy, Paris (FR); Marie-Edith Meyre, Saint Mande (FR)

(73) Assignee: NANOBIOTIX, Paris (FR)

( * ) Notice: Subject to any disclaimer, the term of this patent is extended or adjusted under 35 U.S.C. 154(b) by 223 days.

(21) Appl. No.: 16/472,216

(22) PCT Filed: Dec. 19, 2017

(86) PCT No.: PCT/EP2017/083658
§ 371 (c)(1),
(2) Date: Jun. 21, 2019

(87) PCT Pub. No.: WO2018/115023
PCT Pub. Date: Jun. 28, 2018

(65) Prior Publication Data
US 2019/0351057 A1  Nov. 21, 2019

(30) Foreign Application Priority Data
Dec. 21, 2016  (EP) .................................... 16306753

(51) Int. Cl.
| | |
|---|---|
| *A61K 41/00* | (2020.01) |
| *A61P 25/28* | (2006.01) |
| *A61P 25/16* | (2006.01) |
| *A61N 1/04* | (2006.01) |
| *A61N 1/36* | (2006.01) |
| *A61N 2/00* | (2006.01) |

(52) U.S. Cl.
CPC ...... *A61K 41/0052* (2013.01); *A61K 41/0028* (2013.01); *A61P 25/28* (2018.01); *A61N 1/0456* (2013.01); *A61N 1/36025* (2013.01); *A61N 2/006* (2013.01); *A61P 25/16* (2018.01)

(58) Field of Classification Search
None
See application file for complete search history.

(56) References Cited

U.S. PATENT DOCUMENTS

| | | | | |
|---|---|---|---|---|
| 10,285,934 | B1* | 5/2019 | Sharma | ................. A61K 9/0085 |
| 2013/0317279 | A1* | 11/2013 | Khizroev | ............... A61N 2/006 |
| | | | | 600/12 |
| 2013/0320273 | A1 | 12/2013 | Kotov et al. | |
| 2019/0351231 | A1 | 11/2019 | Meyre et al. | |
| 2020/0086120 | A1 | 3/2020 | Levy et al. | |

FOREIGN PATENT DOCUMENTS

| | | |
|---|---|---|
| WO | WO 2006/126771 | 11/2006 |
| WO | WO 2018/114945 | 6/2018 |
| WO | WO 2018/114988 | 6/2018 |

OTHER PUBLICATIONS

Wang, Y. et al. "Nanomaterial-Enabled Neural Stimulation" *Frontiers in Neuroscience*, Mar. 2016, pp. 1-7, vol. 10, Article 69.
Yong, J. et al."Gold-Nanorod-Assisted Near-Infrared Stimulation of Primary Auditory Neurons" *Adv. Healthcare Mater.*, 2014, pp. 1862-1868, vol. 3, No. 11.
Paviolo, C. et al. "Laser exposure of gold nanorods can induce intracellular calcium transients" *J. Biophotonics.*, 2014, pp. 761-765, vol. 7, No. 10.
Shah, S. et al. "Hybrid upconversion nanomaterials for optogenetic neuronal control" *Nanoscale*, 2015, pp. 16571-16577, vol. 7, No. 40.
Chen, R. et al. "Wireless magnetothermal deep brain stimulation" *Science*, Mar. 12, 2015, pp. 1-7, vol. 347, No. 6229.
Ciofani, G. et al. "Enhancement of Neurite Outgrowth in Neuronal-Like Cells following Boron Nitride Nanotube-Mediated Stimulation" *ACS Nano*, 2010, pp. 6267-6277, vol. 4, No. 10.
Guguru, R. et al. "Magnetoelectric'spin' on stimulating the brain" *Nanomedicine*, 2015, pp. 2051-2061, vol. 10, No. 13.
Marino, A. et al. "Piezoelectric Nanoparticle-Assisted Wireless Neuronal Stimulation" *ACS Nano*, 2015, pp. 7678-7689, vol. 9, No. 7.
Borducchi, D. M. M. et al. "Transcranial Direct Current Stimulation Effects on Athletes' Cognitive Performance: An Exploratory Proof of Concept Trial" *Frontiers in Psychiatry*, Nov. 2016, pp. 1-5, vol. 7, Article 183.

(Continued)

*Primary Examiner* — Susan T Tran
(74) *Attorney, Agent, or Firm* — Saliwanchik, Lloyd & Eisenschenk

(57) ABSTRACT

The present invention relates to the medical field, in particular to the modulation of electrical polarization of neurons. More specifically the present invention relates to a nanoparticle or nanoparticles' aggregate for use for modulating electrical polarization of neurons in a subject, for example for use in prevention or treatment of a neuronal disease in a subject, typically by modulating electrical polarization of neurons in the subject, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate's surface is exposed to an ultrasound source, the nanoparticle's or nanoparticles' aggregate's material is a material enabling acousto-electric transduction, and wherein the nanoparticle or nanoparticles' aggregate is either neutrally charged in the absence of any coating or is coated with a hydrophilic agent conferring a neutral surface charge to the nanoparticle or nanoparticles' aggregate. It further relates to compositions and kits comprising such nanoparticles and/or nanoparticles' aggregates as well as to uses thereof.

12 Claims, 5 Drawing Sheets

(56) References Cited

OTHER PUBLICATIONS

Figure 1:
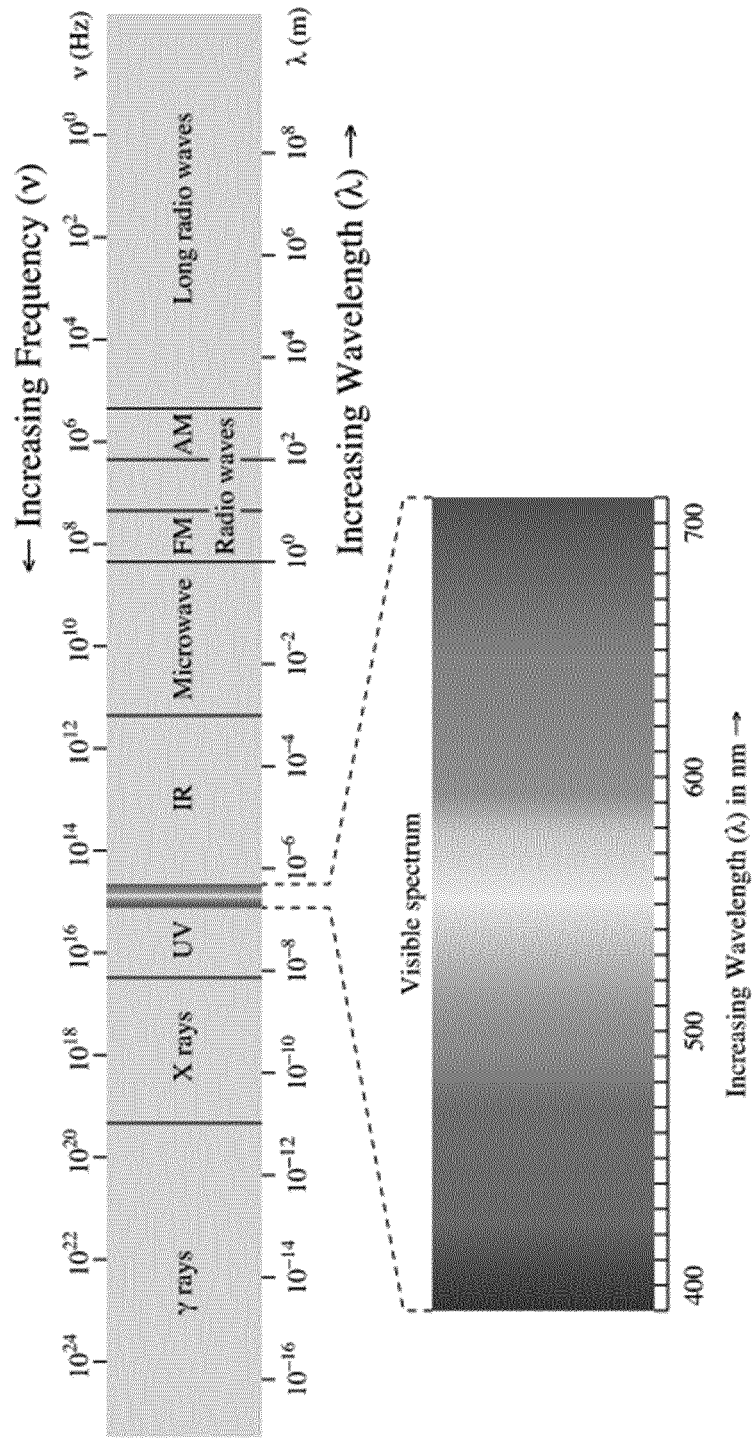

Written Opinion in International Application No. PCT/EP2017/083658, dated Mar. 16, 2018, pp. 1-10.
Written Opinion in International Application No. PCT/EP2017/083533, dated Apr. 16, 2018, pp. 1-7.
Written Opinion in International Application No. PCT/EP2017/083608, dated Mar. 15, 2018, pp. 1-8.
Claims as filed for U.S. Appl. No. 16/472,214, filed Jun. 21, 2019, pp. 1-3.
Claims as filed for U.S. Appl. No. 16/472,215, filed Jun. 21, 2019, pp. 1-3.
Oliveira, P. N. et al. "Synthesis and characterization of structural, microstructural and ferroic properties of $CoFe_2O_4$ nanoparticles and $CoFe_2O_4$:$BaTiO_3$ core-shell nanocomposites" *Integrated Ferroelectrics*, 2016, pp. 88-97, vol. 174, vol. 1.
Zhong, Y. et al. "Facile, Large-Quantity Synthesis of Stable, Tunable-Color Silicon Nanoparticles and Their Application for Long-Term Cellular Imaging" *ACS NANO*, 2015, pp. 5958-5967, vol. 9, No. 6.
*Guangdong Medical Journal*, Nov. 2014, pp. 3586-3588, vol. 35, No. 22.

\* cited by examiner

COATED NANOPARTICLES FOR USE FOR MODULATING ELECTRICAL POLARIZATION OF NEURONS

CROSS-REFERENCE TO RELATED APPLICATION

This application is the U.S. national stage application of International Patent Application No. PCT/EP2017/083658, filed Dec. 19, 2017.

The present invention relates to the medical field, in particular to the modulation of electrical polarization of neurons. More specifically the present invention relates to a nanoparticle or nanoparticles' aggregate for use for modulating electrical polarization of neurons in a subject, for example for use in prevention or treatment of a neuronal disease in a subject, typically by modulating electrical polarization of neurons in the subject, when the nanoparticle or nanoparticles' aggregate is exposed to a light source, a magnetic field, or an ultrasound source, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the nanoparticle or nanoparticles' aggregate is either neutrally charged in the absence of any coating or is coated with a hydrophilic agent conferring a neutral surface charge to the nanoparticle or nanoparticles' aggregate. It further relates to compositions and kits comprising such nanoparticles and/or nanoparticles' aggregates as well as to uses thereof.

BACKGROUND

Neurological disorders are a major health concern (Neurological disorders public health challenges. WHO, 2006). Impairment of neural network function may have different origins. Parkinson's disease is a movement disorder caused by death of dopamine neurons in the substantia nigra, located in the midbrain. Stroke corresponds to a block in the brain's blood supply. Without oxygen, neurons in the affected area die, and the part of the body controlled by those cells cannot function. Huntington's disease is a genetic disorder. Epilepsy is a disorder caused by abnormal excitation of large groups of neurons in various brain regions. Alzheimer's disease is a neurodegenerative disorder characterized by the death of neurons in the hippocampus, cerebral cortex, and other brain regions. The causes of autism spectrum disorders are multifactorial: genetic, environmental, etc.

Neurological disorders can be classified depending on the primary symptoms that affect the patients. Three main types of symptoms are observed: motor disorders, psychiatric (mood/social) disorders and cognitive disorders as further explained herein below.

Motor disorders encompass tremor, hypokinesia such as bradykinesia or dyskinesia, muscle twisting, rigidity, postural instability, gait freezing, etc. Diseases presenting motor disorders include typically Parkinson's disease, dystonia, epilepsy, Huntington's disease and Tourette's syndrome.

Psychiatric disorders constitute a variety of diseases presenting symptoms of mood/social impairments. A non-exhaustive list includes autism spectrum disorders, schizophrenia disorders, bipolar disorders, depressive disorders, anxiety disorders, obsessive-compulsive disorders, substance-related and/or addictive disorders (definition from the *Diagnostic and Statistical Manual of Mental Disorders*, 2013, fifth edition, *the American Psychiatric Association*). Some patients suffering of motor disorders, like Parkinson's disease and dystonia, can develop psychiatric disorders in the late stage of the diseases.

Cognitive disorders are present in many if not all mental disorders (e.g., schizophrenia, bipolar disorders). Only disorders whose core features are cognitive are included in the cognitive disorders category. Cognitive disorders affect the daily life of patients: simple tasks are complicated to achieve. Dementia is a representative cognitive disorder and it is a general term for a decline in mental ability severe enough to interfere with daily life. Alzheimer's disease is a peculiar type of dementia, with a neurodegenerative aspect.

Neurological disorders are, when possible, treated with drugs which play on regulation of the level of neurotransmitters in the brain and on control of interactions with their specific neurotransmitter receptors. The main neurotransmitters involved are: glutamate, γ-aminobutyric acid (GABA), dopamine and acetylcholine. Glutamate and GABA neurotransmitters are of peculiar interest because they play the principal role in increasing (Platt et al., *The Veterinary Journal*, 2007, 173, 278-286: *The role of glutamate in central nervous system health and disease—a review*) and in reducing neuronal excitability, respectively (Holmes et al., *Mental Retardation and Developmental Disabilities*, 1995, 1, 208-219: *Role of glutamate and GABA in the pathophysiology of epilepsy*). Dopamine is involved in several brain functions: control of movement via the basal ganglia (an improper level of dopamine in the basal ganglia results in uncontrolled movements), pleasure reward seeking behavior (disturbance may lead to dysfunctional addiction), cognition (disorders of dopamine in frontal lobes may lead to decline in neurocognitive functions), etc. (Alcaro et al., *Brain Res. Rev.*, 2007, 56(2), 283-321: *Behavioral functions of the mesolimbic dopaminergic system: an affective neuroethological perspective*). Acetylcholine is a neurotransmitter involved in learning and memory at the central nervous system level (Hasselmo et al., *Curr Opin Neurobiol*, 2006, 16(6), 710-715: *The role of acetylcholine in learning and memory*).

A common medication to alleviate the motor symptoms of Parkinson's disease is levodopa, which is transformed in dopamine in the brain and by this way helps in balancing the deficit in dopamine. Levodopa is associated to carbidopa, which helps in avoiding the levodopa transformation in dopamine in all the body. One issue of the levodopa treatment is the "on-off" phenomenon, which results in phases of immobility and incapacity associated with depression alternating with jubilant thaws (Lees et al., *J. Neurology Neurosurgery Psychiatry, Special Supplement*, 1989, 29-37: *The on-off phenomenon*). Non-responsiveness of the late-stage Parkinson's disease patients to this treatment is an issue (Fabbri et al., *Parkinsonism and related disorders*, 2016: *Do patients with late-stage Parkinson's disease still respond to levodopa?*). Other common medications to treat symptoms of neuropsychiatric disorders, like the "positive" symptoms, delusions and hallucinations, in schizophrenia are antipsychotic drugs.

However, therapeutic treatments of neurological disorders' symptoms with these drugs are non-specific, and as such, they may induce severe adverse events. In addition, refractoriness to the used drug may appear.

With advancing comprehension of neuroscience, brain can be thought as an electric network, coding and transmitting information through its electric wires, neurons. Connectivity between neurons is simple and complex at the same time: simple because it lies on influx/efflux of ions inside neurons, which result in action potentials (or "spikes" of electric activity); complex because the brain network is composed of hundreds of billion neurons, which form nodes, hubs and modules that demonstrate coordinated interactions, at various spatial and temporal scales (Fornito et al., *Nature Reviews Neuroscience*, 2015, 16, 159-172: *The connectomics of brain disorders*). Neural communication depends on the anatomical components that connect individual neurons (structure) and on the process of transmitting information (function). Both aspects affect the overall performance of the nervous system. Neuronal interactions are traduced by oscillations of the brain electric activity pattern, which oscillations are measurable typically by electroencephalogram (EEG). Different frequency bands of oscillations are observed: delta, 0.5-3.5 Hz; theta, 3.5-7 Hz; alpha, 8-13 Hz; beta, 15-25 Hz; gamma, 30-70 Hz (Ward et al., *Trends in Cognitive Sciences*, 2003, 7(12), 553-559: *Synchronous neural oscillations and cognitive processes*). Structurally, the most striking neuroanatomical feature of the brain is the abundant connectivity between neurons, which reflects the importance of neural communication. Synchronization of oscillations ("synchrony") between one brain area and another seems to constitute the last level of information coding [first level (neuron): action potentials; second level (neuronal network(s)): neuronal oscillations] by bringing temporal coordination (Engel et al., *Nature Reviews Neuroscience*, 2001, 2, 704-716: *Dynamic predictions: oscillations and synchrony in top-down processing*). Importantly, evidence is emerging that a delicately balanced pattern of synchronization and desynchronization in space and time is fundamental to the functional performance of the nervous system (Schnitzler et al., *Nature Reviews Neuroscience*, 2005, 6, 285-296: *Normal and pathological oscillatory communication in the brain*).

Modulation of the electric activity pattern of neurons (neuromodulation) may be induced through electrical stimulations. The current techniques to produce an electric stimulus into the brain utilize either a direct electric stimulation such as Transcranial Electric Stimulation (TES) or Deep Brain Stimulation (DBS), or the induction of an electric field through the application of an electric current through a magnetic coil such as Transcranial Magnetic Stimulation (TMS).

Recently, non-invasive neural stimulation techniques have been tested, such as the use of light, magnetic field or ultrasounds to directly stimulate neurons.

In order to improve the spatial resolution of the neuronal stimulation at the cellular level, nanomaterials with unique properties have been explored as mediator to convert a wirelessly transmitted primary stimulus to a localized secondary stimulus, primarily electric field or heat, at the nanomaterial-neuron interface (Wang Y. & Guo L. *Frontiers in Neuroscience*. 2016; vol. 10, Article 69, *Nanomaterial-enabled neural stimulation*). Thus, opto-electric transduction has been implemented using quantum dots (semiconductor nanoparticles), as well as opto-thermal transduction using gold nanomaterials, magneto-electric transduction using magneto-electric nanoparticles, magneto-thermal transduction using superparamagnetic nanoparticles and acousto-electric transduction using piezoelectric nanomaterials. Opto-optical transduction using lanthanide-doped nanomaterials has further been implemented (Colombo E. et al., *Frontiers in Neuroscience*. 2016; vol. 10, Article 105, *Nanoparticles: a challenging vehicle for neural stimulation*).

The diverse classes of nanomaterials investigated for neuronal stimulation are still in their early stage of development and some concerns will need to be addressed for their safe use in vivo. Particularly, their biocompatibility is a key aspect to consider.

At the neuron level, nanoparticles have been described to enhance or inhibit electrical excitability of neurons. For instance, zinc oxide, carbon nanotubes and gold nanoparticles were found to enhance electrical excitability of neurons whereas, copper oxide, silver, carbon black, iron oxide and titanium oxide were found to inhibit electrical excitability of neurons (Polak P. & Shefi O. *Nanomedicine: Nanotechnology, Biology and Medicine* 11 (2015) 1467-1479, *Nanometric agents in the service of neuroscience: Manipulation of neuronal growth and activity using nanoparticles*).

Systemic influence studies on neuronal systems of coated silver nanoparticles (cAgNP)—using amphiphilic polymer polyethylene glycol—[cAgNP with hydrodynamic diameter of 13 nm±2 nm (dynamic light scattering technique) and zeta potential of −69 mV (Zetasizer Nano) in pure water]) showed that the nanoparticles induced changes in mechanism affecting excitability (Busse M. et al., *International Journal of Nanomedicine* 2013:8 3559-3572, *Estimating the modulatory effects of nanoparticles on neuronal circuits using computational upscaling*).

Increased excitability of neurons associated with intracellular gold nanoparticles has been described to potentially have deleterious effects on neurons under pathological conditions such as seizure (Jung S, et al., *PLOS ONE* 2014, 9(3) e91360, *Intracellular gold nanoparticles increase neuronal excitability and aggravate seizure activity in the mouse brain*).

The present invention deals with nanoparticles and/or nanoparticles' aggregates (aggregates of nanoparticles) which are either neutrally charged in the absence of any coating or which are coated with a hydrophilic agent conferring a neutral surface charge to the nanoparticle or nanoparticles' aggregate for use for/in modulating electrical polarization of neurons, when the nanoparticle or nanoparticles' aggregate is exposed to a light source/stimulus, a magnetic field or an ultrasound source/stimulus.

The nanoparticle or nanoparticles' aggregate which are either neutrally charged in the absence of any coating or which are coated with a biocompatible agent, typically with a hydrophilic agent, conferring a neutral surface charge to the nanoparticle or nanoparticles' aggregate is particularly advantageous to optimize the use of the nanoparticle or nanoparticles' aggregate for modulating the polarization of neurons when they are exposed to a light source/stimulus, a magnetic field or an ultrasound source/stimulus.

BRIEF DESCRIPTION

Herein advantageously described for the first time is a nanoparticle or nanoparticles' aggregate for use for modulating electrical polarization of neurons in a subject when the nanoparticle or nanoparticles' aggregate is exposed to a light source, a magnetic field, or an ultrasound source, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the nanoparticle or nanoparticles' aggregate is either neutrally charged in the absence of any coating or is coated with a hydrophilic agent conferring a neutral surface charge to the nanoparticle or nanoparticles' aggregate, the neutral charge being of about −10 mV to about +10 mV.

Also herein described is a nanoparticle or nanoparticles' aggregate for use in prevention or treatment of a neuronal disease or at least one symptom thereof in a subject, typically by modulating electrical polarization of neurons in the subject, when the nanoparticle or nanoparticles' aggregate is exposed to a light source, a magnetic field, or an ultrasound source, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the nanoparticle or nanoparticles' aggregate's surface is either neutrally charged in the absence of any coating or is coated with a hydrophilic agent conferring a neutral surface charge to the nanoparticle or nanoparticles' aggregate, the neutral charge being of about −10 mV to about +10 mV.

Also herein described is the use of a nanoparticle or nanoparticles' aggregate as herein described for preparing a composition for preventing or treating a neurological disease as herein described or at least one symptom thereof in a subject in need thereof.

Further herein described is a composition for use for modulating electrical polarization of neurons in a subject when the nanoparticle or nanoparticles' aggregate is exposed to a light source, a magnetic field, or an ultrasound source, wherein the composition comprises, or consists in, nanoparticles and/or nanoparticles' aggregates and a pharmaceutically acceptable support, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the nanoparticle or nanoparticles' aggregate is either neutrally charged in the absence of any coating or is coated with a hydrophilic agent conferring a neutral surface charge to the nanoparticle or nanoparticles' aggregate, the neutral charge being of about −10 mV to about +10 mV.

Also herein described is a composition for use in prevention or treatment of a neuronal disease or at least one symptom thereof in a subject, typically by modulating electrical polarization of neurons in the subject, when the nanoparticle or nanoparticles' aggregate is exposed to a light source, a magnetic field, or an ultrasound source, wherein the composition comprises, or consists in, nanoparticles and/or nanoparticles' aggregates and a pharmaceutically acceptable support, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the nanoparticle or nanoparticles' aggregate is either neutrally charged in the absence of any coating or is coated with a hydrophilic agent conferring a neutral surface charge to the nanoparticle or nanoparticles' aggregate, the neutral charge being of about −10 mV to about +10 mV. Further herein described is a kit comprising at least two distinct nanoparticles and/or nanoparticles' aggregates, each nanoparticle or nanoparticles' aggregate consisting typically of a distinct material selected from a material enabling opto-electric transduction, opto-thermal transduction, opto-optical transduction, magneto-electric transduction, magneto-thermal transduction or acousto-electric transduction, and the nanoparticle or nanoparticles' aggregate being either neutrally charged in the absence of any coating or coated with a hydrophilic agent conferring a neutral surface charge to the nanoparticle or nanoparticles' aggregate, the neutral charge being of about −10 mV to about +10 mV. Also herein described are uses of the kit typically in a method for modulating electrical polarization of neurons in a subject, when the subject is exposed to a light source, a magnetic field, or an ultrasound source. In a particular aspect, the kit is for use in prevention or treatment of/in a method for preventing or treating a neuronal disease or at least one symptom thereof, typically by modulating electrical polarization of neurons in the treated subject, wherein the method comprises a step of exposing the subject who has been administered with the nanoparticle or nanoparticles' aggregate to a light source, a magnetic field, or an ultrasound source as herein described.

Further herein disclosed is a kit as herein described for use in prevention or treatment of a neuronal disease or at least one symptom thereof in a subject, typically by modulating electrical polarization of neurons in the treated subject when the subject is exposed to a light source, a magnetic field, or an ultrasound source.

DETAILED DESCRIPTION

The human nervous system is estimated to consist of roughly 80-120 billion nerve cells (Herculano-Houzel S. *Frontier in Human Neuroscience* (2009), 3(31): 1-11, *The human brain in numbers: a linearly scaled-up primate*

*brain*). The defining characteristic of a neuron (or nerve cell) is its ability to transmit electrical signals in the form of action potentials.

The neuron/nerve cell constitutes the elementary node of the brain. Nerve cells can communicate with each other in a highly-structured manner forming neuronal networks. Neuron communicates via synaptic connections. Within neuron, nanocircuits constitute the underlying biochemical machinery for mediating key neuronal properties such as learning and memory and the genesis of neuronal rhythmicity.

A microcircuit can be formed with just only a few interconnected neurons and can perform sophisticated tasks such as mediate reflexes, process sensory information, initiation of locomotion, and learning and memory mediation. A macrocircuit is a more complex network which consists of multiple imbedded microcircuits. Macrocircuits mediate higher brain functions such as object recognition and cognition. So, multiple levels of networks occupy the nervous system.

Neural Network Excitability

Neurons send messages electrochemically (i.e. chemicals/ions cause an electrical signal). The important ions in the nervous system are sodium and potassium, calcium and chloride. When a neuron is not sending a signal, it is "at rest." When a neuron is at rest, the inside of the neuron is negative relative to the outside. Although the concentrations of the different ions attempt to balance out on both sides of the membrane, they cannot because the cell membrane allows only some ions to pass through channels (ion channels). In addition to these selective ion channels, there is a pump that uses energy to move three sodium ions out of the neuron for every two potassium ions it puts in. Finally, when all these forces balance out, and the difference in the voltage between the inside and outside of the neuron is measured, the resting membrane potential (also "resting potential") of a neuron is about −70 mV. This means that the inside of the neuron is 70 mV less than the outside. At rest, there are relatively more sodium ions outside the neuron and more potassium ions inside that neuron. An action potential (also identified as "spike" or "impulse") occurs when a neuron sends information down an axon, away from the cell body. This means that some event (a stimulus) causes the resting potential to move toward 0 mV. When the depolarization reaches about −55 mV the neuron fires an action potential. If the depolarization does not reach this critical threshold level, then no action potential fires (on/off mechanism). Also, when the threshold level is reached, an action potential of fixed amplitude always fires. Therefore, either the depolarization does not reach the threshold or a full action potential is generated.

Connectivity within and Between Neuronal Networks

There are three connectivity network types that are used to investigate communication within and across the brain. Structural connectivity is based on the detection of the fiber tracks that physically connect the regions of the brain. These are the anatomical network maps that indicate possible pathways that the signals can travel on in the brain. Functional connectivity identifies activity in brain regions that have similar frequency, phase and/or amplitude of correlated activity. Effective connectivity uses the functional connectivity information and goes one step further and determines the direct or indirect influence that one neural system may have over another, more specifically the direction of the dynamic information flow in the brain (Bowyer et al., *Neuropsychiatric Electrophysiology*, 2016, 2(1), 1-12: *Coherence a measure of the brain networks: past and present*). The synchronized activity within a neuronal network can be detected by magnetoencephalogram (MEG), electroencephalogram (EEG), Functional Magnetic Resonance Imaging (FMRI) or Positron Emission Tomography (PET), then image using network connectivity analysis. MEG (Magnetoencephalogram) or EEG (Electroencephalogram) are preferred because they have high temporal resolution to resolve the dynamic flow of information. Connectivity analysis of the brain is performed to map out the communication networks needed for the brain to function. Specific regions in the brain are specialized for processing certain types of information. Imaging techniques have revealed that these regions are connected and communicate with other specialized regions across networks in the brain. Detection of the synchronous activation of neurons can be used to determine the wellbeing or integrity of the functional connectivity in the human brain. Overlaying the functional connectivity maps onto the structural connectivity images and the using direction of information flow derived from effective connectivity provides an all-inclusive understanding of how the brain functions. These techniques help to evaluate treatment therapies based on pre- and post-treatment brain connectivity imaging.

Herein advantageously described for the first time is a nanoparticle or nanoparticles' aggregate for use for modulating electrical polarization of neurons in a subject when the nanoparticle or nanoparticles' aggregate is exposed to a light source, a magnetic field, or an ultrasound source, wherein the nanoparticle or nanoparticles' aggregate is either neutrally charged in the absence of any coating or is coated with a hydrophilic agent conferring a neutral surface charge to the nanoparticle or nanoparticles' aggregate, the neutral charge being of about −10 mV to about +10 mV, and wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction.

The term "modulating electrical polarization of neurons" refers either to a depolarization of the plasma membrane of neurons which activates, induces, excites or triggers an action potential in neurons, or to a hyperpolarization of the plasma membrane of neurons which inhibit any action potential in neurons. The term "modulating electrical polarization of neurons" thus herein either means "inducing a depolarization of the plasma membrane of neurons" or "inducing a hyperpolarization of the plasma membrane of neurons".

Also herein described is a nanoparticle or nanoparticles' aggregate for use in prevention or treatment of a neuronal disease or disorder or at least one symptom thereof in a subject, typically by modulating electrical polarization of neurons in the subject, when the nanoparticle or nanoparticles' aggregate is exposed to a light source, a magnetic field, or an ultrasound source, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii)

when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the nanoparticle or nanoparticles' aggregate's surface is either neutrally charged in the absence of any coating or is coated with a hydrophilic agent conferring a neutral surface charge to the nanoparticle or nanoparticles' aggregate, the neutral charge being of about −10 mV to about +10 mV.

The term "Treatment" refers to therapeutic treatment or measures able to prevent, alleviate or cure a disease, disorder or dysfunctional state as herein described. Such a treatment is intended for a mammal subject, preferably a human subject in need thereof. Are considered as such, the subjects already identified (diagnosed) as suffering from a disease, disorder or dysfunctional state as herein described, or those considered "at risk of developing" such a disease, disorder or dysfunctional state for whom the treatment is a preventive or prophylactic treatment.

In the context of a neuronal disorder, the nanoparticles or nanoparticles' aggregates of the present invention may typically normalize an abnormal neuron polarization when compared to a healthy situation, for example may normalize a reduced neuron polarization, an enhanced neuron polarization, an hyperpolarization of neuron or a loss of neuron polarization (i.e. help the subject to return to a healthy state).

In a particular aspect, the neurological disease or disorder targeted in the context of the invention is selected from Parkinson's disease, Alzheimer's disease, epilepsy, obsessive compulsive disorder, autism spectrum disorder, depression disorder, dystonia, Tourette's syndrome, schizophrenia, stroke, aphasia, dementia, tinnitus, Huntington's disease, essential tremor, bipolar disorder, anxiety disorder, addiction disorder, consciousness vegetative state, for example from Parkinson's disease, Alzheimer's disease, epilepsy, obsessive compulsive disorder, autism spectrum disorder, depression disorder, dystonia, Tourette's syndrome, schizophrenia, stroke, aphasia, dementia, tinnitus, Huntington's disease, essential tremor, bipolar disorder, addiction disorder, consciousness vegetative state, and at least one symptom thereof.

As already explained herein above, neurological diseases or disorders can be classified depending on the primary symptoms that affect the patients which are motor disorders, psychiatric (mood/social) disorders and cognitive disorders as further detailed herein below.

Example of Motor Disorders

Parkinson's Disease

Parkinson's disease (PD) affects about 7 to 10 million people worldwide and it is characterized by tremor, dyskinesia, bradykinesia, gait freezing, etc. PD is a slowly progressive, degenerative disease of the brain. It affects nerve cells in the areas of the brain called the basal ganglia and the substantia nigra. Nerve cells in the substantia nigra produce dopamine, a neurotransmitter that acts as a chemical messenger in brain circuits important for planning and controlling body movement. In PD, the dopamine producing nerve cells of the substantia nigra die off prematurely in some individuals (Corti et al., *Physiol Rev,* 2011, 91, 1161-1218: *What genetics tells us about the causes and mechanisms of Parkinson's disease*). When dopamine receptors in the striatum are not adequately stimulated, parts of the basal ganglia are either under- or over-stimulated. In particular, the subthalamic nucleus (STN) becomes overactive and acts as an accelerator on the globus pallidus internus (GPi). The over-stimulation of the GPi has an over-inhibitory effect on the thalamus, which in turn decreases its output and causes slowing of motion, and rigidity (Guo et al., *Frontiers in Computational Neuroscience,* 2013, 7, 124, 1-11: *Basal ganglia modulation of thalamocortical relay in Parkinson's disease and dystonia*).

The lack of dopamine in PD has been related to excessive oscillatory synchronization in the beta frequency throughout the cortical-basal ganglia motor network. Indeed, the dopamine levels in the basal ganglia are predicted to suppress beta synchrony, which in turn mediate the dopaminergic involvement necessary for movement anticipation (Jenkinson et al., *Trends in Neuroscience,* 2011, 34(12), 611-618: *New insights into the relationship between dopamine, beta oscillations and motor function*). If the level of dopamine in the basal ganglia is not high enough, then there is no control of beta oscillations synchrony anymore, and slowness of movements may appear. Another observation in parkinsonian patients leads to the conclusion that cortical oscillations in the beta band, lead and drive those in the basal ganglia (Lalo et al., *The Journal of Neuroscience,* 2008, 28(12), 3008-3016: *Patterns of bidirectional communication between cortex and basal ganglia during movement in patients with Parkinson disease*).

Deep Brain Stimulation (DBS) can be used to treat the symptoms of tremor and rigidity (Eusebio et al., *J Neurol Neurosurg Psychiatry,* 2011, 82, 569-573: *Deep brain stimulation can suppress pathological synchronization in parkinsonian patients*). The treatment of PD symptoms by DBS is FDA-approved since 2002 (essential tremor since 1997). The electrical stimulation is typically performed in basal ganglia, in the STN and in the GPi. As mentioned above, cortical beta-oscillations are also involved in the pathophysiology of the disease, so transcranial stimulation (such as transcranial magnetic stimulation—TMS) of the cortex could also be used to treat the Parkinson's disease symptoms (Cantello et al., *Brain Research Reviews,* 2002, 38, 309-327: *Transcranial magnetic stimulation and Parkinson's disease*).

Dystonia

Dystonia is a neurological disorder characterized by abnormal, involuntary twisting and turning movements that reflect impaired motor system function. Several forms of dystonia exist, depending on the part of the body affected by the symptoms, on their genetic origin, on the type of neurotransmitter involved, etc. The dystonic Central Nervous System (CNS) exhibits a deficient inhibition, which provokes the loss of reciprocal spinal inhibition between opposing muscles. In the case of upper dystonia for example, an abnormal synchronization of neurons/nerves giving the input signal to the forearm antagonist muscles leads to co-contraction of these antagonist muscles (dystonic symptom) (Farmer et al., *Brain,* 1998, 121, 801-814: *Abnormal motor unit synchronization of antagonist muscles underlies pathological co-contraction in upper limb dystonia*).

The DBS target point showing interesting antidystonic effect is the globus pallidus internus (GPi-DBS). GPi-DBS was approved by FDA in 2003 for patients with chronic, medically intractable dystonia (Hu et al., *Translational Neurodegeneration,* 2014, 3(2), 1-5: *Deep brain stimulation for dystonia*). Stimulation of the ventral intermediate (VIM) nucleus of the thalamus (VIM-DBS) produces much less robust effects. Stimulation using the subthalamic nucleus (STN-DBS) has been experimental. GPi-DBS provides relief of the main symptoms of dystonia, but it can take weeks to months for the therapeutic effects to fully develop (Dressler et al., *J Neural Transm,* 2015, DOI 10.1007/s00702-015-1453-x: *Strategies for treatment of dystonia*).

Epilepsy

Epilepsy is a brain disorder, which affects about 50 million people worldwide, and which is characterized predominantly by recurrent and unpredictable interruptions of normal brain function, called epileptic seizures. Epilepsy is not a singular disease entity but a variety of disorders reflecting underlying brain dysfunction that may result from many different causes (genetic mutation, brain tumors, head trauma, strokes, alcoholism, inflammation of the brain, infections such as meningitis, HIV or viral encephalitis, etc.) (Fisher et al., *Neurology,* 2015, 28(2), 130-135: *Redefining epilepsy*).

An epileptic seizure is defined as a transient occurrence of signs and/or symptoms due to excessive synchronous neuronal activity in the brain (Fisher et al., *Epilepsia,* 2005, 46(4), 470-472: *Epileptic seizures and epilepsy: definitions proposed by the International League Against Epilepsy (ILAE) and the International Bureau for Epilepsy (IBE)*). Cerebral cortex is the primary element in the generation of epileptic seizures: many people are diagnosed with focal frontal lobe or medial temporal lobe seizures (National Institute of Neurological Disorders and Stroke: see Worldwide Website: ninds.nih.gov/disorders/epilepsy/detail epilepsy.htm #3109 7). The identification of areas of elevated local synchrony, or "hypersynchrony", in the cortex suggests that local hypersynchrony may be a marker of seizure-generating areas (Schevon et al., *Neuroimage,* 2007, 35(1), 140-148: *Cortical abnormalities in epilepsy revealed by local EEG synchrony*).

Neurostimulation for treatment of epilepsy can take the form of peripheral nerve stimulation, such as vagus nerve stimulation (VNS); spinal cord stimulation; transcranial brain stimulation (TES or TMS); or deep brain stimulation (DBS). Responsive neurostimulation is another strategy, where stimulation is delivered only when seizure onset is detected. VNS and responsive neurostimulation have both been approved by the FDA for the treatment of certain types of epilepsy in the USA. DBS of the anterior nucleus of the thalamus (ANT) has been approved in countries of the European Union (Fisher et al., *Nature Reviews Neurology,* 2014, 10, 261-270: *Electrical brain stimulation for epilepsy*).

Examples of Psychiatric Disorders (Mood/Social Impairments

Obsessive Compulsive Disorders (OCD)

Obsessive-compulsive disorder (OCD) is a common psychiatric disorder that is often chronic, severe, and extremely debilitating. It is also usually refractory to treatments, with a substantial proportion of patients failing to respond or obtaining only partial relief.

Functional neuroimaging studies have demonstrated dysfunction in the orbitofrontal cortex, basal ganglia and striatum.

A study has shown that acute OCD symptoms may be related to an abnormal high oscillatory activity in the subthalamic nucleus (STN), particularly in the left hemisphere and in the delta-alpha (1-12 Hz) frequency range (Bastin et al., *Cortex,* 2014, 60, 145-150: *Changes of oscillatory activity in the subthalamic nucleus during obsessive-compulsive disorder symptoms: two case reports*). Furthermore, some subthalamic neurons specifically increased their firing rate when doubt occurred during a verification task (Burbaud et al., brain, 2013, 136(1), 304-317: *Neuronal activity correlated with checking behavior in the subthalamic nucleus of patients with obsessive-compulsive disorder*). DBS of the ventral anterior limb of the internal capsule (VC) and adjacent ventral striatum (VS) was approved in the EU for the treatment of severe and highly resistant-treatment OCD (VC/VS-DBS).

Autism Spectrum Disorders

Autism is a neurodevelopmental syndrome that is defined by deficits in social reciprocity and communication, and by unusual restricted, repetitive behaviors. Autism is a disorder that usually begins in infancy, at the latest, in the first three years of life. Autism is a heterogeneous condition (no two children or adults with autism have similar profile), which has led to the concept of "autism spectrum disorder", classifying several levels of the disease according to the degree of language deficit or general cognitive delay, and according to the severity of social or behavioral symptoms (Lord et al., *Neuron,* 2000, 28, 355-363: *Autism spectrum disorders*). At one end of this spectrum, individuals with autism are high functioning, enabling them to live on their own and maintain employment. Individuals characterized as low functioning exhibit more severe symptoms: difficulties for language (or even nonverbal language), poor social communication, self-injurious behavior (SIB), tantrums, and aggression that can be potentially life threatening. An important trend in structural and functional studies of the brain in autism is the involvement of the network for socioemotional processing: the limbic system, the facial processing system and the mirror neuron network. A deficit in synchronization of gamma-band oscillations has been shown to be involved in the apparition of symptoms (Sinha et al., *Neurosurgery Focus,* 2015, 38(6), E3: *Deep brain stimulation for severe autism: from pathophysiology to procedure*).

Two major symptom domains that may require treatment in severe autism are social deficits, including being nonverbal and nonresponsive to speech, and SIB, which can be life threatening. The amygdala seems to play an important role in the pathophysiology of these abnormalities. Altered excitatory or inhibitory control is implicated in the abnormality of autism pathophysiology. Neuromodulation of amygdalar targets via DBS may represent a therapeutic intervention for patients with severe autism. Three cases of DBS treatment were reported in literature. The aim of treatments was mainly to alleviate motor disorders like the stereotypies (repeated movement pattern) and the self-injurious behaviors (SIB) associated to the disease (Sinha et al., *Neurosurgery Focus,* 2015, 38(6), E3: *Deep brain stimulation for severe autism: from pathophysiology to procedure*; Stocco et al., *Parkinsonism and related disorders,* 2014, 20, 1035-1036: *Deep brain stimulation for severe secondary stereotypies*). In one of the three cases, it was reported that DBS in the basolateral nucleus resulted in a significant improvement in autism-related symptoms like social contact, affect modulation and nocturnal sleep (Sturm et al., *Frontiers in Human Neuroscience,* 2013, 6, 341, 1-10).

Schizophrenia

Schizophrenia is a chronic psychiatric illness characterized among others by the following symptoms: positive symptoms, which reflect aberrant mental activity (hallucinations and delusions); negative symptoms, which correspond to the deficiency of a mental function which is normally present (thought disorder, blunting of affect, poverty of speech). Regarding the causes of disability in the lifespan, schizophrenia is located within the top ten.

Prominent ventricular enlargement and increased cerebrospinal fluid on the brain surface suggest that the brain has atrophied. This loss of gray matter and the reduced numbers of synaptic structures on neurons suggest that schizophrenia is a neurodevelopmental disorder, which means that brain abnormalities are already present in first-episode patients (in contrast to neurodegenerative disorder). In schizophrenia patients, the observed impaired neural circuitry has been demonstrated to be due to a failure of gamma-band synchronization (Spencer et al., *The Journal of Neuroscience*, 2003, 23(19), 7407-7411: *Abnormal neural synchrony in schizophrenia*; Gallinat et al., *Clinical Neurophysiology*, 2004, 115, 1863-1874: *Reduced oscillatory gamma-band responses in unmedicated schizophrenic patients indicate impaired frontal network processing*).

Electroconvulsive therapy (ECT), i.e. shock treatment, has been demonstrated to be one of the most successful non-pharmacological treatments in schizophrenia (Payne et al., *J. Psychiatr. Pract.*, 2009, 15(5), 346-368: *Electroconvulsive therapy part I: a perspective on the evolution and current practice of ECT*). It involves the successive application of electrical current to the brain, which provokes seizures comparable to epileptic ones.

Electric stimulation for the symptomatic treatment of schizophrenia is also possible through DBS. For example, DBS of the nucleus accumbens (NAcc) in depression leads to remission of anhedonia, i.e. recovery of hedonic pleasure (Schlaepfer et al., *Neuropsychopharmacology*, 2008, 33, 368-377: *Deep brain stimulation to reward circuitry alleviates anhedonia in refractory major depression*).

Example of Cognitive Disorder

Alzheimer's Disease

Alzheimer's disease (AD) is a neurodegenerative disorder and it leads to progressive loss of mental, behavioral, functional decline and ability to learn. Approximately 200 000 people younger than 65 years with AD comprise the younger onset AD population; 5 million are age 65 years or older.

Recent evidence indicates that cognitive deficits seen in Alzheimer's disease are associated with a functional disconnection of neuro-cognitive networks. Analyses of global EEG synchronization reveal a widespread reduction in the alpha-, beta- and gamma-band synchronization, concomitant with an increase in the delta-band synchronization. In patients with mild Alzheimer's disease, a loss of beta-band synchronization has been shown to correlate with cognitive impairment (Schnitzler et al., *Nature Reviews Neuroscience*, 2005, 6, 285-296: *Normal and pathological oscillatory communication in the brain*). Clinical investigations are ongoing to evaluate the potential of DBS for the treatment of Alzheimer's disease.

Primary Stimulation Sources

When the nanoparticle or aggregate of nanoparticles is exposed to a light source, the nanoparticle's or nanoparticles' aggregate's material is typically selected from a material enabling opto-electric transduction, opto-thermal transduction or opto-optical transduction. In this context, the light source is typically applied through a visible, an ultraviolet (UV) or an infrared (IR) source (cf. FIG. 1).

When the nanoparticle or aggregate of nanoparticles is exposed to a magnetic field, the nanoparticle's or nanoparticles' aggregate's material is typically selected from a material enabling magneto-electric transduction or magneto-thermal transduction. In this context, the magnetic field is typically applied through a low-intensity magnetic field (typically below about 100 Hz), a radio-frequency magnetic field (typically between about 3 kHz and about 300 MHz), or an alternating magnetic field (typically using the following field parameters: amplitudes between about 5 and about 20 kA.m$^{-1}$ and frequencies below 1 MHz).

When the nanoparticle or aggregate of nanoparticles is exposed to an ultrasound source, the nanoparticle's or nanoparticles' aggregate's material is typically a material enabling acousto-electric transduction. The ultrasound source is typically applied using an ultrasound source with any frequency ranging from about 20 kHz to about 20 MHz.

Nanoparticles

Table 1 associates the primary stimulus to an energy source, a secondary stimulus, a nanoparticle type and a target cell.

| Source (primary stimulus) | Secondary stimulus generated by the nanoparticle or nanoparticles' aggregate | Nanoparticle Type | Target cell |
|---|---|---|---|
| Light | Electric field | Semiconductor nanoparticle enabling opto-electric transduction | Neuron/Neural cell |
| Light | Heat | Plasmonic metal nanoparticle enabling opto-thermal transduction | Neuron/Neural cell |
| Light | Light | Lanthanide-doped nanoparticle enabling opto-optical transduction | Neuron/Neural cell expressing one or more light-responsive opsin protein on plasma membrane of this neural cell |
| Magnetic field | Electric field | Magneto-electric nanoparticles enabling magneto-electric transduction | Neuron/Neural cell |
| Magnetic field | Heat | Superparamagnetic nanoparticles enabling magneto-thermal transduction | Neuron/Neural cell |
| Ultrasound | Electric field | Piezo-electric nanoparticles enabling acousto-electric transduction | Neuron/Neural cell |

Composition of Nanoparticles

Opto-Electric Nanoparticle

When the nanoparticle's or nanoparticles' aggregate's material is a material enabling opto-electric transduction, the material is typically a semiconductor material presenting a relatively small energy band gap (Eg) between its valence and conduction bands. Typically, the semiconductor material has a band gap Eg below 3.0 eV, typically when measured at room temperature (25° C.).

In a particular aspect, the material is an intrinsic semiconductor material or an extrinsic semiconductor material as further herein described below.

Intrinsic semiconductor materials typically consist of an element from group IV A of the Mendeleev's periodic table, such as Silicon (Si) or Germanium (Ge), in a mixed composition of elements from groups III and V of the Mendeleev's periodic table, such as AlSb, AlN, GaP, GaN, InP, InN, etc., or in a mixed composition of elements from groups II and VI of the Mendeleev's periodic table, such as ZnSe, ZnTe, CdTe, etc.

Extrinsic semiconductor materials typically comprise, or consist of, an intrinsic semiconductor prepared with a high degree of chemical purity, wherein the intrinsic semiconductor material comprises a dopant. In a particular aspect, when the nanoparticle's or nanoparticles' aggregate's extrinsic semiconductor material consists of an element from group IVA of the Mendeleev's periodic table, it is doped with a charge carrier selected from Al, B, Ga, In and P. Such extrinsic semiconductor material may be either of n-type in which negative charge carriers dominate or of p-type in which positive charge carriers dominate. Typical extrinsic p-type semiconductor material consists of silicon (Si) or germanium (Ge) doped with a charged carrier selected from aluminum (Al), Boron (B), Gallium (Ga) and indium (In); Typical extrinsic p-type semiconductor material consists of silicon (Si) or germanium (Ge) typically doped with phosphorus (P).

Opto-Thermal Nanoparticle

When the nanoparticle's or nanoparticles' aggregate's material is a material enabling opto-thermal transduction, the material is typically a plasmonic metal. Such a plasmonic metal material presents collective oscillations of the free electron gas of a metal at the interface between the metal and a dielectric environment (such as air) in response to incident light, typically at optical frequencies (from visible to infrared). The material enabling opto-thermal transduction is typically selected from gold, silver, platinum and any mixture thereof.

Opto-Optical Nanoparticle

When the nanoparticle's or nanoparticles' aggregate's material is a material enabling opto-optical transduction, the material is typically a lanthanide element-doped material.

The lanthanide element is selected from Lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) or lutetium (Lu), and any mixture thereof. The doping element concentration within the material is typically below 15% (weight by weight).

In a particular aspect, the material enabling opto-optical transduction is a lanthanide element-doped material preferably selected from a lanthanide-doped oxide, a lanthanide-doped mixed-oxide, a lanthanide-doped metal-phosphate, and a lanthanide-doped metal-vanadate.

In a further particular aspect, the oxide is selected from $Y_2O_3$, $Nd_2O_3$, $La_2O_3$ and $SiO_2$.

In another particular aspect, the metal-phosphate is $LuPO_4$.

In another particular aspect the metal-vanadate is $YVO_4$.

In a preferred aspect, the nanoparticle or nanoparticles' aggregate has a lanthanide element selected from Lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) or lutetium (Lu), and a mixture thereof, and the oxide is selected from $Y_2O_3$, $Nd_2O_3$, $La_2O_3$ and $SiO_2$, the metal-phosphate is $LuPO_4$ and/or the metal-vanadate is $YVO_4$.

Magneto-Electric Nanoparticle

When the nanoparticle's or nanoparticles' aggregate's material is a material enabling magneto-electric transduction, the material is typically a magneto-electric material. The magneto-electric material is preferably $CoFe_2O_4@BaTiO_3$.

Magneto-Thermal Nanoparticle

When the nanoparticle's or nanoparticles' aggregate's material is a material enabling magneto-thermal transduction, the material is typically a magnetic material which has a single magnetic domain and present superparamagnetic properties between 15° C. and 45° C. The material enabling magneto-thermal transduction is typically a superparamagnetic oxide such as $Fe_3O_4$ or $Fe_2O_3$ or a superparamagnetic mixed-oxide selected from $NiFe_2O_4$, $MoFe_2O_4$, $MnFe_2O_4$, and $ZnFe_2O_4$.

Acousto-Electric Nanoparticles

When the nanoparticle's or nanoparticles' aggregate's material is a material enabling acousto-electric transduction, the material is typically a piezoelectric material. The piezoelectric material is typically a material presenting a perovskite structure and is preferably selected from barium titanate ($BaTiO_3$), and strontium titanate ($SrTiO_3$), or the piezoelectric material is typically boron nitride (BN).

The Nanoparticle's or Nanoparticles Aggregate's Shape

The nanoparticle or nanoparticles' aggregate shape may typically be a sphere, a rod or a tube. As the shape of the particle or aggregate can influence its "biocompatibility", particle or aggregate having a quite homogeneous shape is preferred. For pharmacokinetic reasons, nanoparticles or aggregates being essentially spherical, round or ovoid in shape are thus preferred. Such a shape also favors the nanoparticle's or aggregate's interaction with cells or uptake by cells. Spherical or round shape is particularly preferred.

The shape of the nanoparticle or aggregate of nanoparticles is typically evaluated using transmission electron microscopy (TEM).

The Nanoparticle's or Nanoparticles Aggregate's Dimension or Size

In the spirit of the invention, the terms "nanoparticle" or "nanoparticles' aggregate" refers to a product, in particular a synthetic product, with a size in the nanometer range, typically between 1 nm and 500 nm.

The term "aggregate of nanoparticles" or "nanoparticles' aggregate" refers to an assemblage of nanoparticles strongly, typically covalently, bound to each other.

Transmission electron microscopy (TEM) can be used to measure the size of the nanoparticle or of the aggregate of nanoparticles. As well, dynamic light scattering (DLS) can be used to measure the hydrodynamic diameter of nanoparticles or nanoparticles' aggregates in solution. These two methods may further be used one after each other to compare size measures and confirm said size. A preferred method is DLS (Ref International Standard ISO22412 Particle Size Analysis—Dynamic Light Scattering, International Organisation for Standardisation (ISO) 2008), whereas the mean hydrodynamic diameter of the nanoparticle or the aggregate of nanoparticles in solution is given in intensity.

Typically, the largest dimension or size is the diameter of a nanoparticle of round or spherical shape, or the longest length of a nanoparticle of ovoid or oval shape.

The largest dimension of a nanoparticle or aggregate as herein defined is typically between about 2 nm and about 250 nm, preferably between about 4 nm or 10 nm and about 100 nm or about 200 nm, even more preferably between about 2 nm and about 150 nm.

The Nanoparticles' or Aggregates of Nanoparticles' Biocompatible Coating

The nanoparticle or aggregate of nanoparticles used in the context of the present invention is either neutrally charged in the absence of any coating or is coated with a biocompatible material (i.e. a coating agent). This biocompatible material is typically a hydrophilic agent conferring a neutral surface charge to the nanoparticle or nanoparticles' aggregate, i.e. a charge between about −10 mV and about +10 mV, for example of about −10 mV, −5 mV, 0 mV, +5 mV or +10 mV. Indeed, when the nanoparticles or nanoparticles' aggregates of the present invention are administered to a subject, nanoparticles or nanoparticles' aggregates which are either neutrally charged in the absence of any coating or which are coated with a biocompatible agent, typically with a hydrophilic agent, conferring a neutral surface charge to the nanoparticles or nanoparticles' aggregates are particularly advantageous to optimize the use of the nanoparticles or nanoparticles' aggregates for modulating the polarization of neurons when exposed to a light source/stimulus, a magnetic field or an ultrasound source/stimulus.

A hydrophilic agent conferring neutral surface charge to the nanoparticle or nanoparticles' aggregate may be an agent displaying a functional group selected from an alcohol (R—OH), an aldehyde (R—COH), a ketone (R—CO—R), an ester (R—COOR), an acid (R—COOH), a thiol (R—SH), a saccharide (for example glucose, fructose or ribose), an anhydride (RCOOOC—R), and a pyrrole. The hydrophilic agent conferring a neutral surface charge to the nanoparticle or nanoparticles' aggregate can be a monomer, a dimer, an oligomer, a polymer or a copolymer. When the agent is an oligomer, it may be an oligosaccharide such as a cyclodextrin. When the agent is a polymer, it may be a polyester (such as a poly(lactic acid) or a polyhydroxyalkanoic acid), a polyether, a polyethylene oxide, a polyethylene glycol, a polyvinylalcohol, a polycaprolactone, a polyvinylpirrolidone, a polysaccharide such as a cellulose, a polypyrrole, etc.

In addition, a hydrophilic agent conferring neutral surface charge to the nanoparticle may be an agent displaying specific groups (R—) able to interact with the surface of the nanoparticle or aggregate of nanoparticles. R is typically selected from a thiol, a silane, a carboxylic and a phosphate group.

When the nanoparticle or aggregate of nanoparticles is a conductor or a semiconductor and a metallic nanoparticle, R is preferably a thiol, a thioether, a thioester, a dithiolane or a carboxylic group. Preferably, the hydrophilic neutral coating agent is selected from a thioglucose, a 2-mercaptoethanol, a 1-thioglycerol, a thiodiglycol and a hydroxybutyric acid.

In a particular aspect, when the nanoparticle or aggregate of nanoparticles is a metallic nanoparticle, R is preferably a thiol, a thioether, a thioester, a dithiolane or a carboxylic group. Preferably, the hydrophilic neutral coating agent is selected from a thioglucose, a 2-mercaptoethanol, a 1-thioglycerol, a thiodiglycol and a hydroxybutyric acid.

When the nanoparticle or aggregate of nanoparticles is an insulator, and an oxide or a mixed-oxide nanoparticle, R is preferably a silane or a phosphate group. Preferably, the hydrophilic neutral coating agent is a hydroxymethyltriethoxysilane, a fructose 6-phosphate or a glucose 6-phosphate compound. In a particular aspect, when the nanoparticle or aggregate of nanoparticles is an oxide, a doped-oxide or a mixed-oxide nanoparticle, R is preferably a silane or a phosphate group. Preferably, the hydrophilic neutral coating agent is a hydroxymethyltriethoxysilane, a fructose 6-phosphate or a glucose 6-phosphate compound.

In a particular aspect, the hydrophilic agent is selected from a poly(lactic acid), a polyhydroxyalkanoic acid, a polyether, a polyethylene oxide, a polyethylene glycol, a polyvinylalcohol, a polycaprolactone, a polyvinylpyrrolidone, a polysaccharide, a polypyrrole, a cyclodextrin, a thioglucose, a 2-mercaptoethanol, a 1-thioglycerol, a thiodiglycol, a hydroxybutyric acid, a hydroxymethyltriethoxysilane, a fructose 6-phosphate and a glucose 6-phosphate.

A hydrophilic agent conferring neutral surface charge to the nanoparticle or nanoparticles' aggregate may be a zwitterionic compound such as an amino acid, a peptide, a polypeptide, a vitamin, a phospholipid (phosphatidylcholine) or a surfactant.

The surface charge of a nanoparticle is typically determined, as well known by the skilled person, by zeta potential measurements, typically in water for a nanoparticles' concentration between 0.2 and 10 g/L, for a pH between 6 and 8, and typically by adding electrolytes at concentrations in water between 0.001 and 0.2 M, for example 0.01 M or 0.15 M. Under the above defined conditions, the surface charge of the nanoparticle or aggregate of nanoparticles is typically comprised between −10 mV and +10 mV, more preferably between −5 mV and +5 mV.

A full biocompatible coating of the nanoparticle or aggregate may be advantageous in the context of the present invention in order to avoid any electrical charge on the nanoparticle's surface, when the nanoparticle presents a hydrophilic neutral surface charge. The "full coating" implies the presence of a very high density/compactness of biocompatible molecules able to create at least a complete monolayer on the surface of the particle.

The biocompatible coating allows in particular the nanoparticle's or nanoparticles' aggregate's stability in a fluid, such as a physiological fluid (blood, plasma, serum, etc.) or any isotonic media or physiologic medium required for a pharmaceutical administration.

Stability may be confirmed by dry extract quantification using a drying oven and measured on a nanoparticle suspension prior and after filtration, typically on a 0.45 µm filter.

Advantageously, the coating preserves the integrity of the particle in vivo, ensures or improves the biocompatibility thereof, and facilitates an optional functionalization thereof (for example with spacer molecules, biocompatible polymers, targeting agents, proteins, etc.).

The biocompatible nanoparticle or aggregate of nanoparticles of the invention should neither dissolve and release toxic species following in vivo administration (i.e. at physiological pH) nor present redox behavior.

Also herein disclosed is the use of a nanoparticle or nanoparticles' aggregate as herein described for preparing a composition for preventing or treating a neuronal disease as herein described or at least one symptom thereof in a subject in need thereof.

Another particular object herein described relates to a composition, in particular a pharmaceutical composition, comprising nanoparticles and/or nanoparticles aggregates such as defined or described hereinabove, preferably together with a pharmaceutically acceptable carrier or vehicle.

In particular, herein described is a composition for use for modulating electrical polarization of neurons in a subject when the nanoparticle or nanoparticles' aggregate is exposed to a light source, a magnetic field, or an ultrasound source as herein described, wherein the composition comprises, or consists of, nanoparticles and/or nanoparticles' aggregates and a pharmaceutically acceptable support, and wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the (typically each) nanoparticle or nanoparticles' aggregate is either neutrally charged in the absence of any coating or is coated with a hydrophilic agent conferring a neutral surface charge to the nanoparticle or nanoparticles' aggregate, the neutral charge being of about −10 mV to about +10 mV, as herein above explained.

Further herein described is a composition for use in prevention or treatment of a neuronal disorder as herein described or at least one symptom thereof in a subject, typically by modulating electrical polarization of neurons in the subject, when the nanoparticle or nanoparticles' aggregate is exposed to a light source, a magnetic field, or an ultrasound source, wherein the composition comprises, or consists of, nanoparticles and/or nanoparticles' aggregates and a pharmaceutically acceptable support, wherein i) when the nanoparticle or nanoparticles' aggregate is exposed to a light source, the nanoparticle's or nanoparticles' aggregate's material is selected from a material enabling opto-electric transduction, opto-thermal transduction or opto-optical transduction, ii) when the nanoparticle or nanoparticles' aggregate is exposed to a magnetic field, the nanoparticle's or nanoparticles' aggregate's material is selected from a material enabling magneto-electric transduction or magneto-thermal transduction, iii) when the nanoparticle or nanoparticles' aggregate is exposed to an ultrasound source, the nanoparticle's or nanoparticles' aggregate's material is a material enabling acousto-electric transduction, and wherein the nanoparticle or nanoparticles' aggregate is either neutrally charged in the absence of any coating or is coated with a hydrophilic agent conferring a neutral surface charge to the nanoparticle or nanoparticles' aggregate, the neutral charge being of about −10 mV to about +10 mV.

In a preferred aspect, the composition comprises, or consists of, at least two distinct nanoparticles and/or nanoparticles' aggregates, each nanoparticle or nanoparticles' aggregate consisting of a distinct material typically selected from a material enabling opto-electric transduction, opto-thermal transduction, opto-optical transduction, magneto-electric transduction, magneto-thermal or acousto-electric transduction, and wherein the (typically each) nanoparticle or nanoparticles' aggregate is either neutrally charged in the absence of any coating or is coated with a hydrophilic agent conferring a neutral surface charge to the nanoparticle or nanoparticles' aggregate.

The composition can be in the form of a solid, liquid (particles in suspension), aerosol, gel, paste, and the like. Preferred compositions are in a liquid or a gel form. Particularly preferred compositions are in liquid form.

The pharmaceutically acceptable support or carrier which is employed can be any classical support for the skilled person, such as for example a saline, isotonic, sterile, or buffered solution and the like.

The composition can also comprise stabilizers, sweeteners, surfactants, polymers and the like.

It can be formulated for example as ampoule, aerosol, bottle, tablet, capsule, by using techniques of pharmaceutical formulation known by the skilled person.

The nanoparticles or nanoparticles' aggregates of the invention can be administered to the subject using different possible routes such as intra-cranial, intra venous (IV), airways (inhalation), intra-thecal, intra-ocular or oral route (per os), preferably using intra-cranial or intra-thecal.

Repeated injections or administrations of nanoparticles or nanoparticles' aggregates can be performed, when appropriate.

The herein described nanoparticles or nanoparticles' aggregates and compositions comprising such nanoparticles or nanoparticles' aggregates are for use in a subject, typically for use in an animal, preferably in a mammal, even more preferably in a human being, whatever its age or sex.

Typical quantity(ies) of nanoparticles or aggregates of nanoparticles to be administered in the cerebral cortex of the subject is(are) between $10^5$ and $10^{15}$, preferably between $10^7$ and $10^{14}$, more preferably between $10^9$ and $10^{12}$. Also, typical quantity(ies) of nanoparticles or aggregates of nanoparticles to be administered in the cerebral cortex of the subject is(are) between $10^2$ and $10^{12}$ nanoparticles or aggregates of nanoparticles per $cm^3$.

Typical quantity(ies) of nanoparticles or aggregate of nanoparticles to be administered in the deep brain of the subject is(are) between $10^4$ and $10^{14}$, preferably between $10^6$ and $10^{12}$, more preferably between $10^8$ and $10^{11}$. Also, typical quantity(ies) of nanoparticles or aggregates of nanoparticles to be administered in the deep brain of the subject is(are) between $10^1$ and $10^{11}$ nanoparticles or aggregates of nanoparticles per $cm^3$.

In the context of the invention, exposing nanoparticles or nanoparticles' aggregates to a light source, a magnetic field, or an ultrasound source is equivalent to exposing a subject who has been administered with nanoparticles or nanoparticles' aggregates to a light source, a magnetic field, or an ultrasound source.

Also herein described is a method for modulating in vivo electrical polarization of neurons in a subject, wherein the method comprises a step of administering anyone of the herein described nanoparticles or nanoparticles' aggregates to the subject and a step of exposing said subject to a light source, a magnetic field, or an ultrasound source.

Further herein described is a method for preventing or treating a neuronal disease or at least one symptom thereof in a subject, typically by modulating electrical polarization of neurons in the treated subject, wherein the method comprises a step of administering anyone of the herein described nanoparticles or nanoparticles' aggregates to the subject and a step of exposing said subject to a light source, a magnetic field, or an ultrasound source.

A further object herein described relates to a kit comprising at least two distinct nanoparticles and/or nanoparticles' aggregates as herein described, each nanoparticle or nanoparticles' aggregate consisting of a distinct material typically selected from a material enabling opto-electric transduction, opto-thermal transduction, opto-optical transduction, magneto-electric transduction, magneto-thermal transduction, or acousto-electric transduction, and wherein the (typically each) nanoparticle or nanoparticles' aggregate is either neutrally charged in the absence of any coating or is coated with a hydrophilic agent conferring a neutral surface charge to the nanoparticle or nanoparticles' aggregate as herein described, the neutral charge being of about −10 mV to about +10 mV.

In a particular embodiment, the kit comprises, in distinct containers, distinct nanoparticles or nanoparticles aggregates as herein described (which are intended to be contacted, typically mixed, either in situ, i.e. on the target site, or in vitro or ex vivo before deposition of the mixture on the target site).

Also herein described is the use, in vivo, in vitro or ex vivo, of such a kit in a method for modulating the electrical polarization of neurons in a subject as herein described, for example in a method for preventing or treating a neurological disease as herein described or at least one symptom thereof in a subject, typically by modulating the electrical polarization of neurons in the subject.

The present invention aims at modulating the electrical polarization of neurons thanks to the use of nanoparticles or nanoparticles' aggregates exposed to a light stimulus/source, a magnetic field, or an ultrasound stimulus/source.

In a particular aspect, the kit is for use in prevention or treatment of/in a method for preventing or treating a neuronal disease as herein described or at least one symptom thereof, typically by modulating electrical polarization of neurons in the treated subject, wherein the method comprises a step of exposing the subject who has been administered with the nanoparticle or nanoparticles' aggregate to a light source, a magnetic field, or an ultrasound source as herein described.

Further herein disclosed is a kit as herein described for use in prevention or treatment of a neuronal disease or at least one symptom thereof in a subject, typically by modulating electrical polarization of neurons in the treated subject when the subject is exposed to a light source, a magnetic field, or an ultrasound source.

The present nanoparticles or aggregates of nanoparticles of the invention now advantageously allows an enhanced spatial resolution (focality) of the light source, the magnetic field, or the ultrasound source where the nanoparticles are localized. In particular aspects, herein described nanoparticles allow in addition an enhanced safety profile thanks to their neutral surface charge (increasing its therapeutic effect)

The examples which follow and their corresponding figures illustrate the invention without limiting the scope thereof.

FIGURES

FIG. 1. The electromagnetic spectrum.

Figure 2:
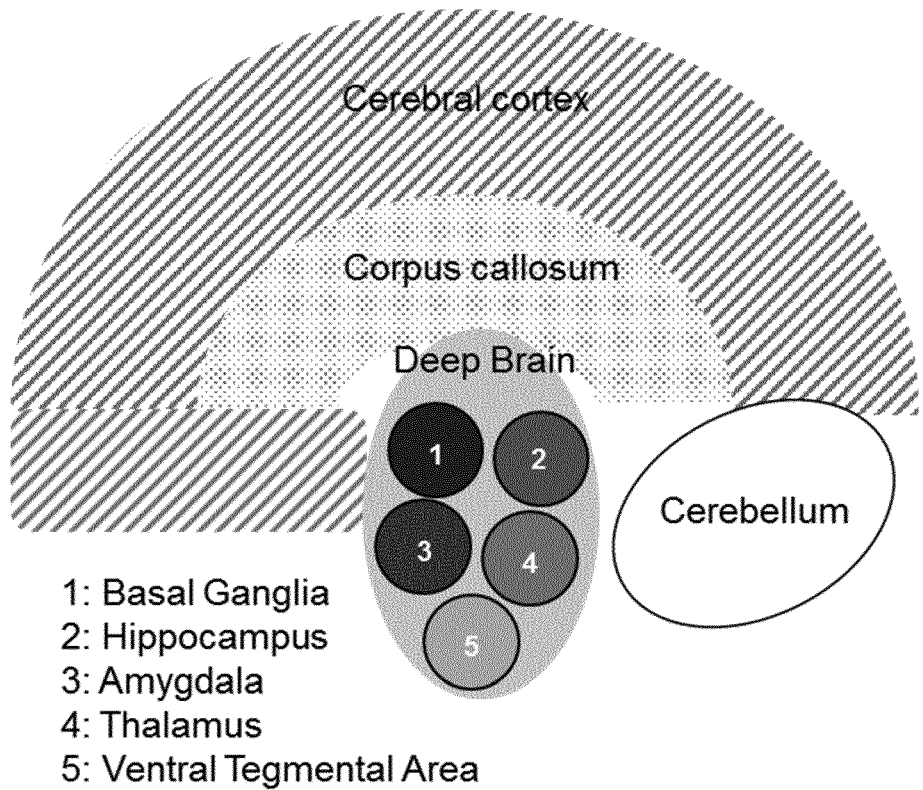

FIG. 2. Schematic representation of the brain (sagittal plane).

Figure 3:
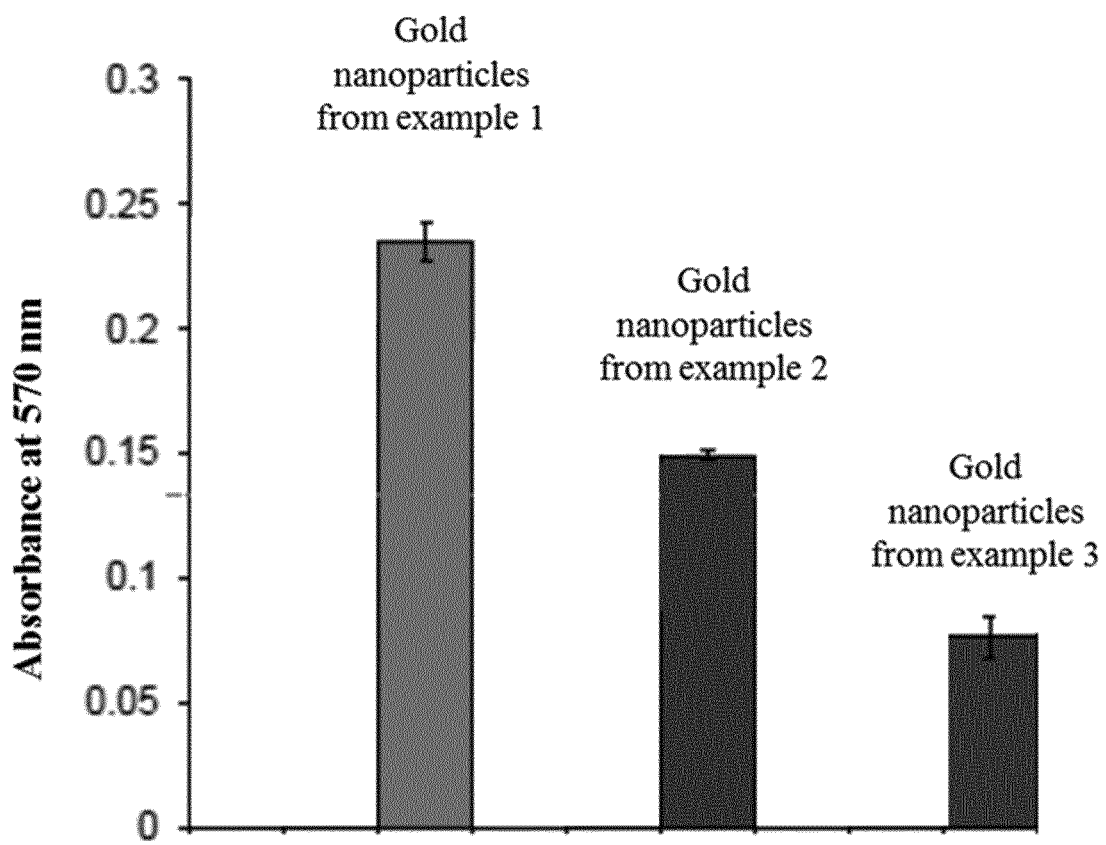

FIG. 3. Metabolic activity assessment using the MTT assay on neuron cells treated with gold nanoparticles coated with a coating conferring (i) a neutral surface charge of −3.4 mV to nanoparticles from example 1, (ii) a negative surface charge of −27.0 mV to nanoparticles from example 2, and (iii) a positive surface charge of +26.1 mV to nanoparticles from example 3. The absorbance is measured at 570 nm. The cellular health is correlated with the Absorbance value at 570 nm: the higher the Absorbance value, the higher the cellular health. The absorbance value is higher for gold nanoparticles from example 1 than for gold nanoparticles from example 2 (about a 2-fold increase) or gold nanoparticles from example 3 (about a 3-fold increase).

Figure 4:
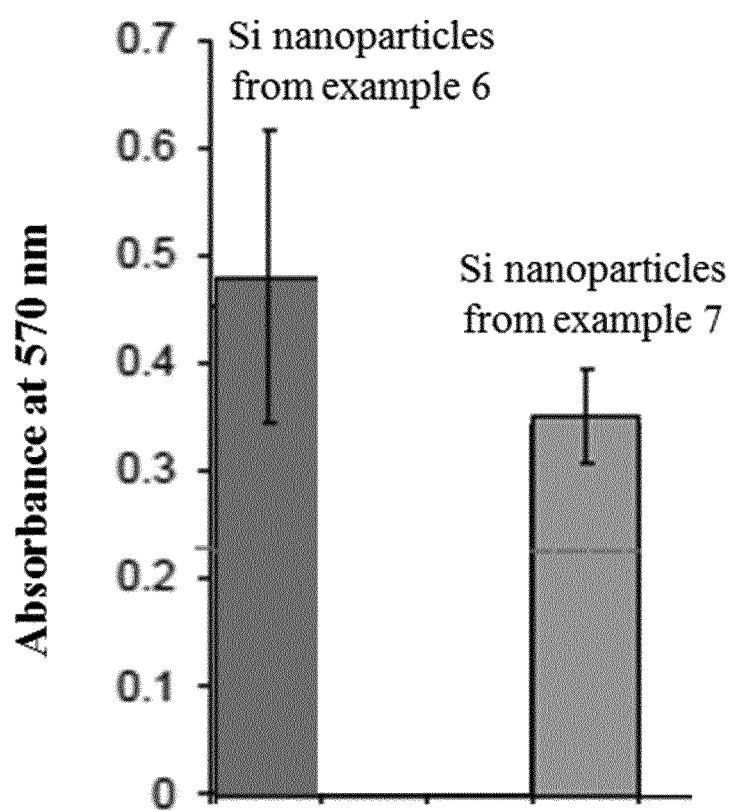

FIG. 4. Metabolic activity assessment using the MTT assay on neuron cells treated with silicon nanoparticles coated with a coating conferring (i) a neutral surface charge of −4.5 mV to nanoparticles from example 6, and (ii) a positive surface charge of +16.0 mV to nanoparticles from example 7. The absorbance is measured at 570 nm. The cellular health is correlated with the Absorbance value at 570 nm: the higher the Absorbance value, the higher the cellular health. The absorbance value is higher for Si nanoparticles from example 6 than for Si nanoparticles from example 7 (about a 1.5-fold increase).

Figure 5:
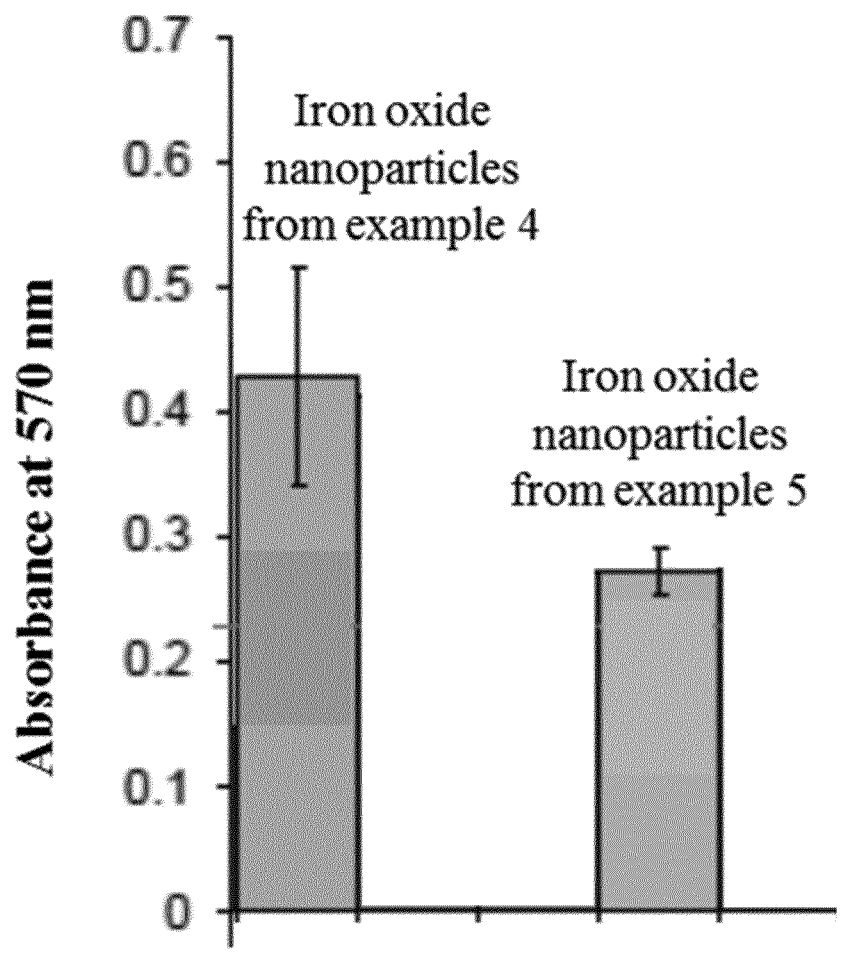

FIG. 5. Metabolic activity assessment using the MTT assay on neuron cells treated with iron oxide nanoparticles coated with a coating conferring (i) a neutral surface charge of +8.5 mV to nanoparticles from example 4, and (ii) a negative surface charge of −36.4 mV to nanoparticles from example 5. The absorbance is measured at 570 nm. The cellular health is correlated with the Absorbance value at 570 nm: the higher the Absorbance value, the higher the cellular health. The absorbance value is higher for $Fe_2O_3$ nanoparticles from example 4 than for $Fe_2O_3$ nanoparticles from example 5 (about a 1.5-fold increase).

EXAMPLES

In Vitro Studies of Neurons

At the neuron level, patch clamp technique is very useful for detecting action potentials, as it allows simultaneous direct measurement and control of membrane potential of a neuron.

This technique is used to assess the effects of nanoparticles on a single neuron.

In Vitro Studies of a Network of Neurons

Multi-electrode arrays (MEAs) permit stimulation and recording of a large number of neurons (neuronal network). Dissociated neuronal cultures on MEAs provide a simplified model in which network activity can be manipulated with stimulation sequences through the array's multiple electrodes. This technique is very useful to assess physiologically relevant questions at the network and cellular levels leading to a better understanding of brain function and dysfunction.

Cellular health can also typically be monitored using the 3-(4,5-dimethylthiazol-2-yl)-2,5-diphenyltetrazolium bromide (MTT) assay. The MTT cytotoxicity assay uses metabolic activity as a readout to describe cellular health.

This technique is used typically to assess the functional effect of nanoparticles on neuronal network(s).

Example 1

Nanoparticles Enabling Opto-Thermal Transduction: Synthesis of Gold Nanoparticles Coated with a Biocompatible Coating Conferring a Neutral Surface Charge to Gold Nanoparticles Gold nanoparticles were synthesized by reducing a gold chloride salt ($HAuCl_4$) with a capping agent (sodium citrate) (protocol was adapted from G. Frens Nature Physical Science 241 (1973) 21). In a typical experiment, $HAuCl_4$ solution was heated to boiling. Subsequently, sodium citrate solution was added. The resulting solution was maintained under boiling for an additional period of 5 minutes.

A 0.22 μm filtration (filter membrane: poly(ether sulfone) (PES)) of the nanoparticles' suspension was performed and gold concentration in suspension was determined by a UV-visible spectroscopy assay at 530 nm.

A surface coating was performed using α-methoxy-ω-mercaptopoly(ethylene glycol) 20 kDa ("thiol-PEG20 kDa"). A sufficient amount of "thiol-PEG 20 kDa" was added to the nanoparticles' suspension to reach at least half a monolayer coverage (2.5 molecules/nm$^2$) on the gold nanoparticle surface. pH was adjusted between 7 and 7.2, and the nanoparticles' suspension was stirred overnight.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The hydrodynamic diameter of the so obtained biocompatible gold nanoparticles in suspension was found equal to 122.5 nm, with a polydispersity index (dispersion of the nanoparticles' population in size) of 0.15.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −3.4 mV.

Example 2

Nanoparticles Enabling Opto-Thermal Transduction: Synthesis of Gold Nanoparticles Coated with a Biocompatible Coating Conferring a Negative Surface Charge to Gold Nanoparticles Gold nanoparticles were prepared as described in example 1 (same gold inorganic core).

A 0.22 µm filtration on PES membrane filter was performed and gold concentration in suspension was determined by a UV-visible spectroscopy assay at 530 nm.

A surface coating was performed using meso-2, 3-dimercaptosuccinic acid (DMSA). A sufficient amount of DMSA was added to the nanoparticles' suspension to reach at least half a monolayer coverage (2.5 molecules/nm$^2$) on the surface of gold nanoparticles. pH was adjusted between 7 and 7.2, and the nanoparticles' suspension was stirred overnight.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The hydrodynamic diameter of the so obtained nanoparticles in suspension was equal to 127.4 nm, with a polydispersity index (dispersion of the nanoparticles' population in size) of 0.54.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −27.0 mV.

Example 3

Nanoparticles Enabling Opto-Thermal Transduction: Synthesis of Gold Nanoparticles Coated with a Biocompatible Coating Conferring a Positive Surface Charge to Gold Nanoparticles Gold nanoparticles were prepared as described in example 1 (same gold inorganic core).

A 0.22 µm filtration on PES membrane filter was performed and gold concentration in suspension was determined by a UV-visible spectroscopy assay at 530 nm.

A surface coating was performed using poly(diallyldimethylammonium) chloride (PDADAC). A sufficient amount of PDADAC was added to the nanoparticles' suspension to reach at least half a monolayer coverage (2.5 molecules/nm$^2$) on the surface of gold nanoparticles. pH was adjusted between 7 and 7.2, and the nanoparticles' suspension was stirred overnight.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The hydrodynamic diameter of the so obtained nanoparticles in suspension was equal to 94.1 nm, with a polydispersity index (dispersion of the nanoparticles' population in size) of 0.51.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to +26.1 mV.

Example 4

Nanoparticles Enabling Magneto-Thermal Transduction: Synthesis of Iron Oxide Nanoparticles Coated with a Biocompatible Coating Conferring a Neutral Surface Charge to Iron Oxide Nanoparticles Iron oxide ($Fe_2O_3$) nanoparticles were synthesized by co-precipitation of iron (III) nitrate ($Fe(NO_3)_3$) and iron (II) chloride ($FeCl_2$) with sodium hydroxide (NaOH) at a basic pH, in a reacting medium with a high ionic strength. The resulting nanoparticles' suspension was washed three times with water by centrifugation.

A 0.22 µm filtration on PES membrane filter was performed and ($Fe_2O_3$) nanoparticles' concentration was determined by a colorimetric assay in UV-visible spectroscopy.

A coating was prepared using silane-poly(ethylene) glycol 20 kDa ("Si-PEG 20 kDa"). A sufficient amount of "Si-PEG 20 kDa" was added to the nanoparticles' suspension to reach at least half a monolayer coverage (2.5 molecules/nm$^2$) on the surface of iron oxide nanoparticles. The nanoparticles' suspension was stirred overnight and subsequently the pH was adjusted to 7.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 102.5 nm, with a polydispersity index (dispersion of the nanoparticles' population in size) of 0.11.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to +8.5 mV.

Example 5

Nanoparticles Enabling Magneto-Thermal Transduction: Synthesis of Iron Oxide Nanoparticles Coated with a Biocompatible Coating Conferring a Negative Surface Charge to Iron Oxide Nanoparticles Iron oxide ($Fe_2O_3$) nanoparticles were prepared as described in example 4 (same $Fe_2O_3$ inorganic core).

A 0.22 μm filtration on PES membrane filter was performed and ($Fe_2O_3$) nanoparticles' concentration was determined by a colorimetric assay in UV-visible spectroscopy.

A coating was prepared using sodium hexametaphosphate. A sufficient amount of sodium hexametaphosphate was added to the nanoparticles' suspension to reach at least 1 molecule of sodium hexametaphosphate/$nm^2$ on the surface of iron oxide nanoparticles. The nanoparticles' suspension was stirred overnight and subsequently the pH was adjusted to 7.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 81.5 nm, with a polydispersity index (dispersion of the nanoparticles' population in size) of 0.16.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −36.4 mV.

Example 6

Nanoparticles Enabling Opto-Electric Transduction: Silicon Nanoparticles Coated with a Biocompatible Coating Conferring a Neutral Surface Charge to Silicon Nanoparticles Silicon (Si) nanoparticles' suspension (50 g/L) with 5 nm size were obtained from Meliorum Technologies Inc.

A 0.22 μm filtration on PES membrane filter was performed and the (Si) nanoparticles' concentration was determined by drying the suspension to a powder and weighing the as-obtained mass.

A coating was prepared using silane-poly(ethylene) glycol 20 kDa ("Si-PEG 20 kDa"). A sufficient amount of "Si-PEG 20 kDa" was added to the nanoparticles' suspension to reach at least half a monolayer coverage (2.5 molecules/$nm^2$) on the surface of silicon nanoparticles. The nanoparticles' suspension was stirred overnight and subsequently the pH was adjusted to 7.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −4.5 mV.

Example 7

Nanoparticles Enabling Opto-Electric Transduction: Silicon Nanoparticles Coated with a Biocompatible Coating Conferring a Positive Surface Charge to Silicon Nanoparticles Silicon (Si) nanoparticles were obtained from Meliorum Technologies Inc. as described in example 6 (same Si inorganic core).

A 0.22 μm filtration on PES membrane filter was performed and the (Si) nanoparticles' concentration was determined by drying the suspension to a powder and weighing the as-obtained mass.

A coating was prepared using 3-aminopropyltriethoxysilane (APS). A sufficient amount of APS was added to the nanoparticles' suspension to reach at least half a monolayer coverage (2.5 molecules/$nm^2$) on the surface of silicon nanoparticles. The nanoparticles' suspension was stirred overnight and subsequently the pH was adjusted to 7.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to +16.0 mV.

Example 8

Assessment of Cytotoxicity in Midbrain/Frontal Cortex Mouse Neurons Induced by Nanoparticles from Examples 1, 2 and 3 Via the MTT Assay The MTT cytotoxicity assay uses metabolic activity as a readout to describe cellular health. The 3-(4,5-dimethylthiazol-2-yl)-2,5-diphenyltetrazolium bromide (MTT) assay measures the mitochondrial activity of viable cells by quantifying the conversion of the tetrazolium salt to its formazan product. The conversion of the tetrazolium salt to its formazan product is a marker reflecting viable cell metabolism.

Material and Methods

Primary Cell Culture

Midbrain/frontal cortex tissue was harvested from embryonic day 14 chr:NMRI mice (Charles River). Mice were sacrificed by cervical dislocation. Tissue was dissociated by enzymatic digestion (133,3 Kunitz units/ml DNase; 10 Units/ml Papain) and mechanical trituration, counted, vitality controlled, and plated in a 20 μl drop of DMEM containing laminin (10 μg/ml), 10% fetal bovine serum and 10% horse serum on 48-wells microelectrode array neurochips (Axion Biosystems Inc.) coated for 1 hour with Polyethyleneimine (PEI, 50% in Borate buffer), washed and air-dried. Cultures were incubated at 37° C. in a 10% $CO_2$ atmosphere until ready for use. Culture media were replenished two times a week with DMEM containing 10% horse serum.

MTT Assay

The mouse midbrain/frontal cortex neuronal cell cultures were cultured for 4 weeks. After 4 weeks, the nanoparticles' suspensions from examples 1, 2 and 3 (800 μM) were added to the wells. Twenty-four (24 h) post nanoparticles' suspensions treatment, the medium was changed to avoid direct interaction of the 3-[4,5-dimethylthiazol-2-yl]-2,5 diphenyl tetrazolium bromide (MTT) reagent with the nanoparticles. Forty-eight hours (48 h) post nanoparticles' suspensions treatment, cells were treated with the MTT reagent at 50 μg/ml, then incubated for 120 minutes at 37° C. and 10% $CO_2$, and subsequently lysed in 200 μl lysis buffer (DMSO, 0.4 M acetic acid). Lysates were transferred into 96-well plates and optical density was recorded at 570 nm to quantify the MTT-specific absorbance. Values were plotted after blank value (lysis buffer) substraction.

FIG. 3 presents the Absorbance measured at 570 nm for neuron cells treated with gold nanoparticles coated with a coating conferring (i) a neutral surface charge of −3.4 mV to nanoparticles from example 1, (ii) a negative surface charge of −27.0 mV to nanoparticles from example 2, and (iii) a positive surface charge of +26.1 mV to nanoparticles from example 3. The absorbance value is higher for gold nanoparticles from example 1 than for gold nanoparticles from example 2 (about a 2-fold increase) or gold nanoparticles from example 3 (about a 3-fold increase).

These results demonstrate that the neuron health is enhanced in neuron cultures treated with the nanoparticles described in the present application when said nanoparticles are coated with an hydrophilic coating agent conferring them a neutral surface charge, typically a neutral charge above −10 mV and below +10 mV, rather than a surface charge above +10 mV or below −10 mV.

Therefore, an enhanced safety profile and an increased therapeutic effect is expected when using the nanoparticles described in the present application provided that they are coated with an hydrophilic coating agent conferring them a neutral surface charge.

Example 9

Assessment of Long-Term Cytotoxicity in Midbrain/Frontal Cortex Mouse Neurons Induced by Nanoparticles from Examples 6 and 7 Via the MTT Assay Material and Methods
Primary Cell Culture Midbrain/frontal cortex tissue was harvested from embryonic day 14 chr:NMRI mice (Charles River). Mice were sacrificed by cervical dislocation. Tissue was dissociated by enzymatic digestion (133,3 Kunitz units/ml DNase; 10 Units/ml Papain) and mechanical trituration, counted, vitality controlled, and plated in a 20 µl drop of DMEM containing laminin (10 µg/ml), 10% fetal bovine serum and 10% horse serum on 48-wells microelectrode array neurochips (Axion Biosystems Inc.) coated for 1 hour with Polyethyleneimine (PEI, 50% in Borate buffer), washed and air-dried. Cultures were incubated at 37° C. in a 10% $CO_2$ atmosphere until ready for use. Culture media were replenished two times a week with DMEM containing 10% horse serum.

MTT Assay

The mouse midbrain/frontal cortex neuronal cell cultures were cultured for 4 weeks. After 4 weeks, the nanoparticles' suspensions from examples 6 and 7 (200 µM) were added to the wells. Twenty-four (24 h) post nanoparticles' suspensions treatment, the medium was changed to avoid direct interaction of the 3-[4,5-dimethylthiazol-2-yl]-2,5 diphenyl tetrazolium bromide (MTT) reagent with the nanoparticles. Fourteen (14) days post nanoparticles' suspensions treatment, cells were treated with the MTT reagent at 50 µg/ml, then incubated for 120 minutes at 37° C. and 10% $CO_2$, and subsequently lysed in 200 µl lysis buffer (DMSO, 0.4 M acetic acid). Lysates were transferred into 96-wells plates and optical density was recorded at 570 nm to quantify the MTT-specific absorbance. Values were plotted after blank value (lysis buffer) substraction.

FIG. 4 presents the Absorbance measured at 570 nm for neuron cells treated with Si nanoparticles coated with a coating conferring (i) a neutral surface charge of −4.5 mV to nanoparticles from example 6, and (ii) a positive surface charge of +16.0 mV to nanoparticles from example 7. The absorbance value is higher for Si nanoparticles from example 6 than for Si nanoparticles from example 7 (about a 1.5-fold increase).

These results demonstrate that the neuron health is enhanced in the neuron cultures treated with the nanoparticles described in the present application when they are coated with an hydrophilic coating agent conferring them a neutral surface charge, typically a neutral surface charge above −10 mV and below +10 mV, rather than a surface charge above +10 mV or below −10 mV.

Therefore, an enhanced safety profile and an increased therapeutic effect is expected when using the nanoparticles described in the present application provided that they are coated with an hydrophilic coating agent conferring them a neutral surface charge.

Example 10

Assessment of Long-Term Cytotoxicity in Midbrain/Frontal Cortex Mouse Neurons Induced by Nanoparticles from Examples 4 and 5 Via the MTT Assay Material and Methods
Primary Cell Culture Midbrain/frontal cortex tissue was harvested from embryonic day 14 chr:NMRI mice (Charles River).

Mice were sacrificed by cervical dislocation. Tissue was dissociated by enzymatic digestion (133,3 Kunitz units/ml DNase; 10 Units/ml Papain) and mechanical trituration, counted, vitality controlled, and plated in a 20 µl drop of DMEM containing laminin (10 µg/ml), 10% fetal bovine serum and 10% horse serum on 48-wells microelectrode array neurochips (Axion Biosystems Inc.) coated for 1 hour with Polyethyleneimine (PEI, 50% in Borate buffer), washed and air-dried. Cultures were incubated at 37° C. in a 10% $CO_2$ atmosphere until ready for use. Culture media were replenished two times a week with DMEM containing 10% horse serum.

MTT Assay

The mouse midbrain/frontal cortex neuronal cell cultures were cultured for 4 weeks. After 4 weeks, the nanoparticles' suspensions from examples 4 and 5 (200 µM) were added to the wells. Twenty-four (24 h) post nanoparticles' suspensions treatment, the medium was changed to avoid direct interaction of the 3-[4,5-dimethylthiazol-2-yl]-2,5 diphenyl tetrazolium bromide (MTT) reagent with the nanoparticles. Fourteen (14) days post nanoparticles' suspensions treatment, cells were treated with the MTT reagent at 50 µg/ml, then incubated for 120 minutes at 37° C. and 10% $CO_2$, and subsequently lysed in 200 µl lysis buffer (DMSO, 0.4 M acetic acid). Lysates were transferred into 96-wells plates and optical density was recorded at 570 nm to quantify the MTT-specific absorbance. Values were plotted after blank value (lysis buffer) substraction.

FIG. 5 presents the Absorbance measured at 570 nm for neuron cells treated with iron oxide nanoparticles coated with a coating conferring (i) a neutral surface charge of +8.5 mV to nanoparticles from example 4, and (ii) a negative surface charge of −36.4 mV to nanoparticles from example 5. The absorbance value is higher for $Fe_2O_3$ nanoparticles from example 4 than for $Fe_2O_3$ nanoparticles from example 5 (about a 1.5-fold increase).

These results demonstrate that the neuron health is enhanced in the neuron cultures treated with the nanoparticles described in the present application when they are coated with an hydrophilic coating agent conferring them a neutral surface charge, typically a neutral surface charge above −10 mV and below +10 mV, rather than a surface charge above +10 mV or below −10 mV.

Therefore, an enhanced safety profile and an increased therapeutic effect is expected when using the nanoparticles described in the present application provided that they are coated with an hydrophilic coating agent conferring them a neutral surface charge.

The invention claimed is:

1. A method for treating a neuronal disease in a subject by modulating electrical polarization of neurons in the subject, wherein the method comprises a) administering a composition of nanoparticle or nanoparticle aggregate to the subject, wherein i) when the nanoparticle or nanoparticle aggregate is exposed to a light source, the nanoparticle or nanoparticle aggregate material is selected from a material enabling opto-electric transduction, opto-thermal transduction or opto-optical transduction, or ii) when the nanoparticle or nanoparticle aggregate is exposed to a magnetic field, the nanoparticle or nanoparticle aggregate material is a material enabling magneto-electric transduction or magneto-thermal transduction, or iii) when the nanoparticle or nanoparticle aggregate is exposed to an ultrasound source, the nanoparticle or nanoparticle aggregate material is a material enabling acousto-electric transduction, and wherein the nanoparticle or nanoparticle aggregate surface is either neutrally charged in the absence of any coating or coated with a hydrophilic agent conferring a neutral surface charge to the nanoparticle or nanoparticle aggregate, the neutral charge being of about −10 mV to +10 mV, and b) exposing the subject to a light source, a magnetic field, or an ultrasound source, thereby modulating electrical polarization of neurons in the subject, and wherein the nanoparticle or nanoparticle aggregate of step a) is at least two distinct nanoparticles and/or nanoparticle aggregates, each nanoparticle or nanoparticle aggregate consisting of a distinct material selected from a material enabling opto-electric transduction, opto-thermal transduction, opto-optical transduction, magneto-electric transduction, magneto-thermal transduction or acousto-electric transduction, and the nanoparticle or nanoparticle aggregate surface being optionally coated with a hydrophilic agent conferring a neutral surface charge to the nanoparticle or nanoparticle aggregate.

2. The method according to claim 1, wherein the material enabling opto-electric transduction is a semiconductor material with a band gap Eg below 3.0 eV.

3. The method according to claim 1, wherein the material enabling opto-thermal transduction is a plasmonic metal material.

4. The method according to claim 1, wherein the material enabling opto-optical transduction is a lanthanide element-doped material selected from a lanthanide-doped oxide, a lanthanide-doped mixed-oxide, a lanthanide-doped metal-phosphate, and a lanthanide-doped metal-vanadate.

5. The method according to claim 1, wherein the material enabling magneto-thermal transduction is a superparamagnetic material.

6. The method according to claim 1, wherein the material enabling acousto-electric transduction is a piezoelectric material.

7. The method according to claim 1, wherein the hydrophilic agent conferring a neutral surface charge to the nanoparticle or nanoparticle aggregate displays a functional group selected from an alcohol (R—OH), an aldehyde (R—COH), a ketone (R—CO—R), an ester (R—COOR), an acid (R—COOH), a thiol (R—SH), a saccharide, an anhydride (RCOOOC—R), and a pyrrole.

8. The method according to claim 1, wherein the hydrophilic agent is selected from a poly(lactic acid), a polyhydroxyalkanoic acid, a polyether, a polyethylene oxide, a polyethylene glycol, a polyvinylalcohol, a polycaprolactone, a polyvinylpyrrolidone, a polysaccharide, a polypyrrole, a cyclodextrin, a thioglucose, a 2-mercaptoethanol, a 1-thioglycerol, a thiodiglycol, a hydroxybutyric acid, a hydroxymethyltriethoxysilane, a fructose 6-phosphate and a glucose 6-phosphate.

9. The method according to claim 1, wherein the subject is a human being.

10. A method for treating a neuronal disease in a subject by modulating electrical polarization of neurons in the subject, wherein the method comprises a) administering a composition to the subject, the composition comprising nanoparticles and/or nanoparticle aggregates and a pharmaceutically acceptable support, wherein i) when the nanoparticle or nanoparticle aggregate is exposed to a light source, the nanoparticle or nanoparticle aggregate material is selected from a material enabling opto-electric transduction, opto-thermal transduction or opto-optical transduction, or ii) when the nanoparticle or nanoparticle aggregate is exposed to a magnetic field, the nanoparticle or nanoparticle aggregate material is a material enabling magneto-electric transduction or magneto-thermal transduction, or iii) when the nanoparticle or nanoparticle aggregate is exposed to an ultrasound source, the nanoparticle or nanoparticle aggregate material is a material enabling acousto-electric transduction, and wherein the nanoparticle or nanoparticle aggregate surface is either neutrally charged in the absence of any coating or coated with a hydrophilic agent conferring a neutral surface charge to the nanoparticle or nanoparticle aggregate, the neutral charge being of about −10 mV to +10 mV, and b) exposing the subject to a light source, a magnetic field, or an ultrasound source, thereby modulating electrical polarization of neurons in the subject, and wherein the composition comprises at least two distinct nanoparticles and/or nanoparticle aggregates, each nanoparticle or nanoparticle aggregate consisting of a distinct material selected from a material enabling opto-electric transduction, opto-thermal transduction, opto-optical transduction, magneto-electric transduction, magneto-thermal transduction or acousto-electric transduction, and the nanoparticle or nanoparticle aggregate surface being optionally coated with a hydrophilic agent conferring a neutral surface charge to the nanoparticle or nanoparticle aggregate.

11. The method according to claim 10, wherein the subject is a human being.

12. The method according to claim 1, wherein the material enabling magneto-electric transduction is $CoFe_2O_4@BaTiO_3$.

* * * * *